United States Patent [19]

Zegers de Beyl et al.

[11] Patent Number: 4,551,133
[45] Date of Patent: Nov. 5, 1985

[54] PATIENT CONTROLLED MEDICATION INFUSION SYSTEM

[75] Inventors: Rene H. Zegers de Beyl, Glendale; Stephen J. Coble, Sunland, both of Calif.

[73] Assignee: American Hospital Supply Corporation, Evanston, Ill.

[21] Appl. No.: 600,663

[22] Filed: Apr. 16, 1984

[51] Int. Cl.$^4$ ............................................. A61M 5/00
[52] U.S. Cl. ..................................... 604/66; 604/67; 128/DIG. 12
[58] Field of Search ..................................... 604/65–67, 604/246; 128/DIG. 12, DIG. 13

[56] References Cited

U.S. PATENT DOCUMENTS

| | | | |
|---|---|---|---|
| 4,231,354 | 11/1980 | Kurtz et al. | 604/66 X |
| 4,275,727 | 6/1981 | Keeriszanto | 604/66 |
| 4,280,494 | 7/1981 | Cosgrove et al. | 604/66 X |
| 4,392,849 | 7/1983 | Petre et al. | 604/66 |
| 4,409,966 | 10/1983 | Lambecht et al. | 604/66 X |
| 4,457,751 | 7/1984 | Rodler | 604/67 X |
| 4,475,901 | 10/1984 | Kraegen et al. | 604/66 X |

Primary Examiner—Edward M. Coven
Attorney, Agent, or Firm—Roger A. Williams

[57] ABSTRACT

A medication infusion system which includes an infusion line for introducing medication to a peripheral vein of a patient. The infusion system includes a pump for delivering the medication and a pressure transducer within the infusion line for converting sensed fluid pressure waves to electrical signals. An amplifier is provided within the system for increasing the strength of the electrical signal. A gain control amplifier is electrically connected within the system for maintaining the electrical signal at a predetermined amplitude regardless of input variations. A tracking filter is provided within the system to provide an electrical signal representative of the patient's respiration rate over a preselected full clinical respiration rate range. A microprocessor is provided within the system for deriving from the electrical signal a control signal for controlling the operation of the pump. The microprocessor includes the ability to determine the presence or absence of the electrical signal representative of the patient's respiration rate, a comparator for comparing the rate signal with a preselected respiration rate and a storage capability for storing the rates and preselected rate values. The system further includes a motor control for providing a signal to the pump for actuating the pump in preselected increments when directed by the microprocessor.

18 Claims, 8 Drawing Figures

RAW SIGNAL

Fig. 4

SIGNAL AFTER BANDPASS FILTER

Fig. 5

SIGNAL AFTER 0 CROSSING DETECTOR

PATIENT CONTROLLED MEDICATION INFUSION SYSTEM

BACKGROUND OF THE INVENTION

The invention herein relates to an assembly for the infusion of medication into a patient in response to the patient's demand and based upon the patient's physiological condition. The invention herein is particularly related to a patient controlled analgesia system wherein the patient can request the administration of an analgesic agent, but the delivery of such analgesic agent is controlled by the system based upon the patient's physiological conditions, and more specifically, the patient's respiration rate. The system herein can also detect infiltration and/or occlusion of the infusion line leading to a peripheral vein of the patient for introducing medication to such peripheral vein.

Pain is often associated with the postoperative care patient. In the past, the most common method of delivering analgesic medication to a patient has been the administration of such medication by an attendant, such as a nurse, after the patient has requested such medication. In such procedures, patients have to bear unnecessary pain until an attendant becomes available to deliver the medication. The administration of such medication is usually performed with the introduction of the analgesic agent in a relatively greater than needed dosage, which will be sufficient to reduce the pain for a sufficiently longer time than necessary. The medication and dosage is dictated by a doctor's prescription. The patient receives an initially large dose of the analgesic agent which is usually more than the amount required to reduce the pain, but which is a sufficiently large amount so as to provide prolonged relief for a predetermined period. A problem associated with delivering such an initially large dosage of medication is that the volume may be sufficiently great that the patient, especially the post-operative patient, can have depressed physiological conditions, such as respiration rate and heart rate. Thus, the attendant or attending nurse must monitor the patient's respiration rate and heart rate, to assure that the desired levels are maintained.

It would be desirable to provide an automatic medication introduction rate control system which would provide a sufficient amount of medication to a patient upon demand to overcome any pain, but which would monitor the physiological conditions of the patient so as to prevent introduction of medication when the patient's physiological conditions warrant not introducing such medication. It would also be desirable to have a system which would provide an indication when occlusion and/or infiltration of the infusion line has occurred. It would be greatly desirable to provide such systems which could be directly connected to the patient's venous system, and thereby be compatible with standard intravenous (IV) administration sets.

SUMMARY OF THE INVENTION

The invention herein is directed to a medication introduction rate control system, and more particularly, a patient controlled medication delivery system. The system herein provides monitoring the respiration rate and heart rate of a patient from a peripheral vein. The system also provides the ability for detecting infiltration and/or occlusion in the peripheral infusion line used to intravenously infuse fluids into the patient through a catheter inserted in a peripheral vein.

The medication introduction rate control system herein, when connected to a peripheral vein of a patient, provides the patient the ability to request and receive delivery of medication as needed and as can be tolerated by the patient. If the patient makes too many demands for medication in too short a time interval, the system is designed to ignore the demands and wait for the preselected time interval before delivering the medication. The system continuously monitors the patient's physiological condition, and through such continuous monitoring can determine infiltration, occlusion, and depressed physiological conditions which, upon being determined by the system, stops any further delivery of medication and warns the attendants for the patient that such conditions have occurred so that appropriate remedial action can be taken.

The system herein can be used for delivery of any medication, but is particularly useful for delivery of analgesic agents and will be described with regard to such an end use. A patient, such as a postoperative patient in pain, can make a request of the system for a dosage of medication, such as an analgesic. The system recognizes that a request for medication has been received. The system monitors the physiological condition of the patient, such as the respiration rate and/or heart rate. If the physiological conditions are at an acceptable level that a medication dosage is appropriate as can be preset in the system, then the system directs a pump to deliver the prescribed dosage of medication.

The system is capable of monitoring the physiological conditions of the patient as the system includes a pressure transducer which is in fluid wave pressure communication, with the fluid being infused into the peripheral vein of the patient through an infusion line. The pressure transducer can be in direct or indirect contact with such fluid. The signal from the pressure transducer is amplified and then filtered to provide a signal which is representative of the patient's physiological condition, such as respiration and heart rate. The representative signal is directed to a microprocessor which compares the representative signal to a preselected respiration and/or heart rate which can be inputted by a physician or attendant into a memory associated with the microprocessor. The microprocessor compares the representative signal to a previously determined representative signal to determine whether the respiration and/or heart rate are being depressed or remaining stable or time. The microprocessor also detects the presence of a signal to determine if there is infiltration or occlusion of the infusion line. Based upon such comparisons, the microprocessor can provide a control signal to a motor associated with a pump assembly for administering the medication. The control signal will either drive the motor in an incremental step to provide the prescribed dosage of medication, or will provide a signal to stop the motor, thereby denying the request for medication by not activating the pump assembly for delivering a dosage of medication.

BRIEF DESCRIPTION OF THE DRAWINGS

The invention herein will be described with regard to the accompanying drawings which illustrate a preferred embodiment of the invention only and are not to be construed as limiting.

DESCRIPTION OF THE PREFERRED EMBODIMENT

Figure 1:
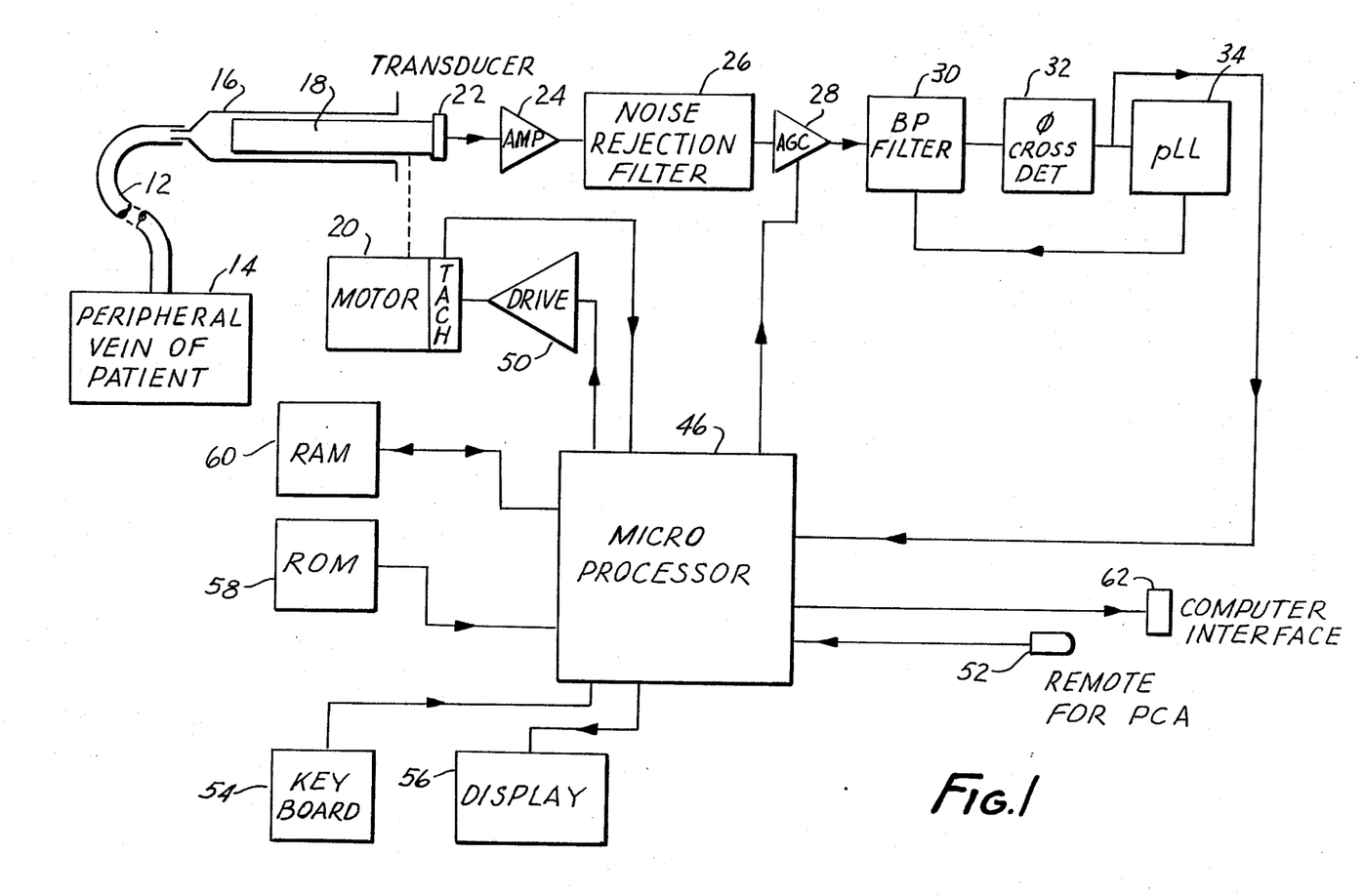
FIG. 1 is a block diagram of a circuit for the patient controlled medication infusion system herein.

The patient controlled medication infusion system herein will be described with regard to the accompanying drawings. In FIG. 1, there is illustrated a circuit for a patient controlled medication infusion system for controlling the introduction of medication to a peripheral vein of a patient. Although referred to as patient controlled, the system is a medication delivery system which can deliver medication to the patient upon demand by the patient, and when the appropriate patient physiological conditions are met as monitored and determined by the system. In FIG. 1, an infusion line 12 is schematically represented as being in contact with a peripheral vein of a patient 14. The infusion line can be any appropriate infusion line commonly used with IV administration sets and state of the art medication delivery systems. The system herein is an improvement over presently available medication rate control systems, as the system herein can be part of an IV administration set as to both its physiological monitoring assembly and medication delivery assembly. An advantage of the system is that many patients in need of medication delivery are provided with IV administration.

The infusion line is in fluid-flow communication with a medication reservoir 16 which contains the medication to be administered to the patient. The medication reservoir 16 can be any reservoir capable of retaining the medication to be delivered, such as a syringe 18. The syringe 18, along with a motor 20, comprises an infusion pump assembly which delivers medication through the infusion line to the peripheral vein of the patient. Various infusion pumps are commercially available. Such pumps can include a pump housing which can receive a prefilled syringe containing the medication to be administered. Some infusion pumps contain reservoirs which can be filled with the appropriate medication. Preferably, the motor for actuating the infusion pump assembly is a stepper motor which moves incrementally. The incremental steps of the motor can be coordinated with the pump; i.e., syringe, to move the syringe plunger a measured distance, thereby enabling delivery of predetermined increments or aliquots of the medication. The motor 20, upon actuation, thereby provides a prescribed dosage of the medication to the patient.

A pressure transducer 22 is in fluid pressure wave communication with the medication to be administered. The pressure transducer 22 can be in either direct or indirect fluid pressure wave communication with the medication present in the infusion line 12, or in the medication reservoir 16. In direct communication, the pressure transducer has its pressure sensing element in fluid-flow communication with the fluid medication to be administered. There may be an electrically nonconducting barrier between the pressure transducer and fluid, which barrier transmits sensed fluid pressure waves in the fluid line to the pressure transducer. The pressure transducer can be indirect fluid pressure wave communication by having the pressure transducer separated from the fluid medication in the fluid infusion line by a barrier across which the fluid waves do not propagate. For example, the pressure transducer can be attached to a portion of the syringe which can translate fluid pressure in the syringe to the pressure transducer as movement. For example, the pressure transducer can be in pressure sensing communication with the syringe plunger, which syringe plunger can move in detectable movements corresponding to pressure waves in the fluid or medication reservoir. The detectable movements of the syringe plunger can be detected by the pressure transducer and thereby provide an indirect measurement of the fluid pressure waves in the fluid medication present in the infusion line. Many pressure transducers are commercially available and such commercially available models are acceptable. Monolithic silicone pressure sensors such as described in U.S. Pat. No. 4,317,126 can also be used. A preferred pressure sensored transducer is SPX-100D, available from Motorola, Inc.

Figure 3:
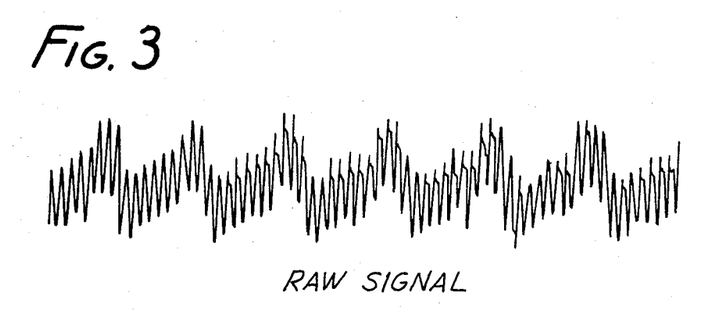
FIG. 3 is a representation of a raw signal of the pressure wave sensed at the peripheral vein of a patient.

The electric signal produced by the pressure transducer is amplified by an amplifier 24. An amplifier is desirable to amplify the signal from the pressure transducer as the fluid pressure waves are generally quite small, and with a sensitive pressure transducer, the electrical signal produced is correspondingly small. The unfiltered signal from the pressure transducer 22 is represented by the raw signal shown in FIG. 3. The amplified electrical signal is filtered through a first noise rejection filter 26 which can be a low pass filter.

The signal from the low pass filter 26 passes to an automatic gain control amplifier 28 (AGC). The microprocessor 46, which will be more fully explained hereinafter, continuously tracks the amplitude of the signal and keeps the amplitude constant. The microprocessor varies the gain of the automatic gain control amplifier 28 with the amplitude of the incoming signal. The amplitude of the incoming signal can change due to the patient's movement. For example, if the patient raises or lowers his arm, the static pressure in the peripheral vein will go up or down respectively. Therefore, there would be a variation in signals. It is, therefore, best to maintain the gain constant or keep the signal constant by varying the gain through an amplifier.

The automatic gain control also provides one method for determining infiltration and/or occlusion. The microprocessor is programmed to measure the amount of gain control needed to apply to the signal. When the amount of gain goes beyond a certain threshold towards a maximum gain which is preselected in the microprocessor, then the microprocessor recognizes that the signal has been lost. The loss of the signal is indicative of infiltration and/or occlusion of the infusion line. It will be appreciated by those skilled in the art that partial occlusion and/or infiltration can also be detected by the system as there is some signal loss in such circumstances. It is important to detect occlusion or infiltration in the infusion line as patency of the line is critical to the delivery of the medication to the patient and loss of the vein means delivery which is less than ideal and not beneficial to the patient. It is, therefore, important to maintain the IV patent within the patient's peripheral vein.

Figure 4:
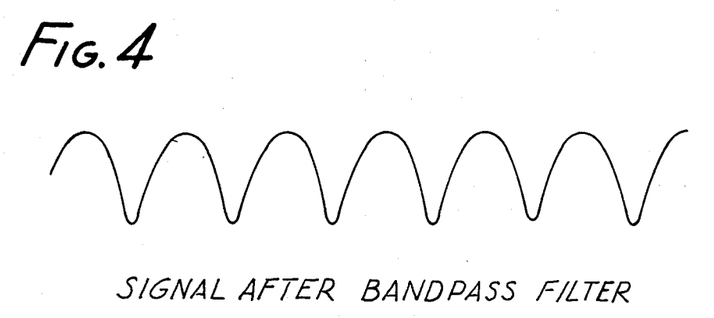
FIG. 4 is a representation of a signal after it has been partially filtered by the system herein.
Figure 5:
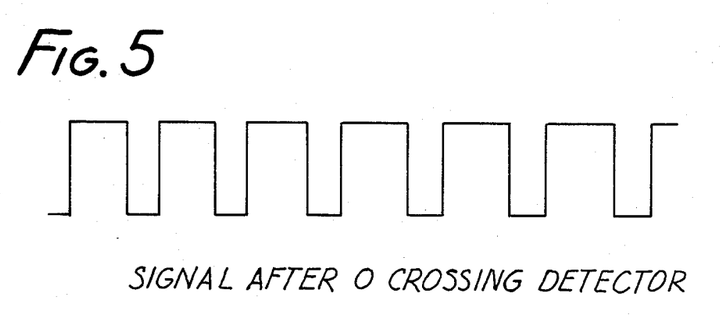
FIG. 5 is a representation of the signal from the patient's peripheral vein after being filtered by the system herein after processing in the zero crossing detector and before being received by the microprocessor.

The electric signal passes from the automatic gain control 28 (AGC) to the band pass filter 30. The band pass filter filters the signal and provides a signal representative of the patient's respiration rate as can be seen in FIG. 4. The signal then is passed through a zero crossing detector 32. The resultant signal after passing through the zero crossing detector is represented by the schematic signal shown in FIG. 5.

Figure 2:
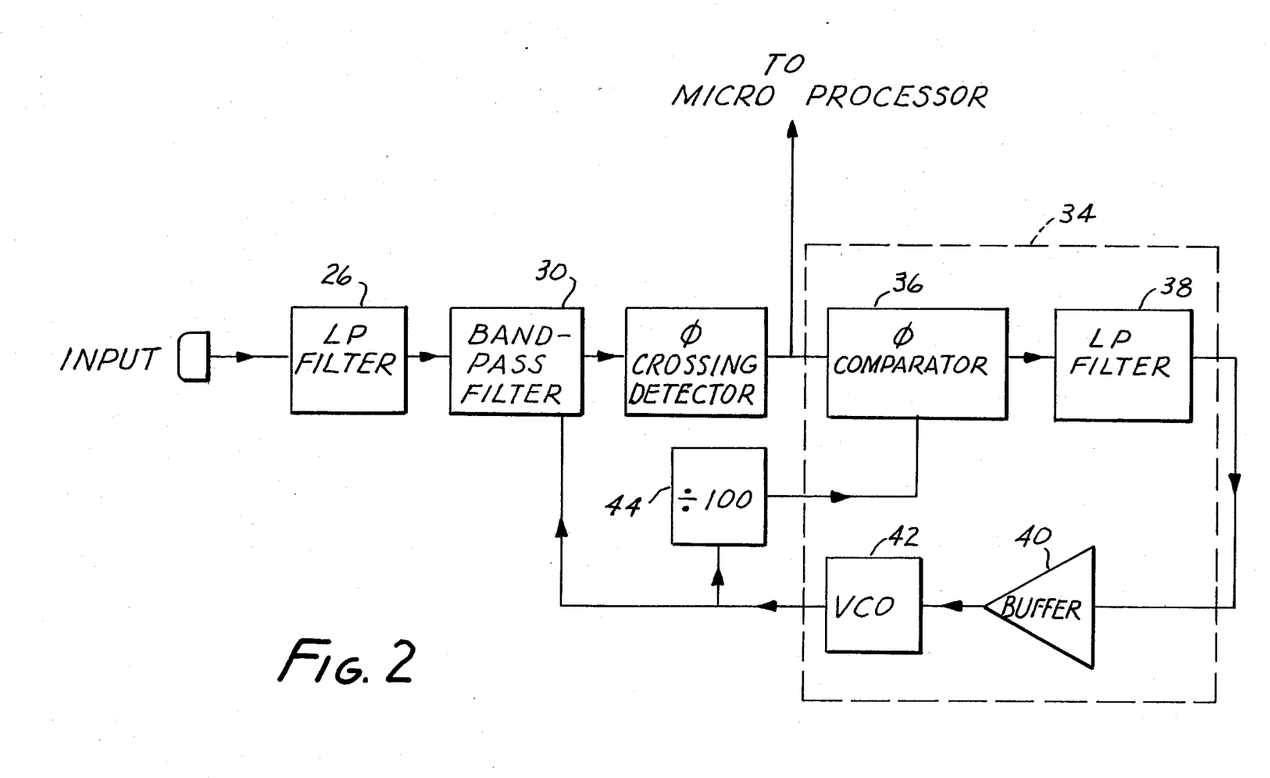
FIG. 2 is a block diagram of a circuit representing the phase lock loop portion of the system illustrated in FIG. 1.

The electric signal after passing through the zero crossing detector is then processed through a phase lock loop 34. The electric signal passing through the zero crossing detector is representative of the respiratory rate of the patient and/or can be representative of the heart rate of the patient. The phase lock loop circuit is shown in FIG. 2. With regard to FIG. 2, the electric signal passing from the zero crossing detector is first passed to a phase comparator 36. The phase comparator compares the phase of the signal against a reference. The phase lock loop also includes a voltage control oscillator 42 and a low pass filter 38. The signal flowing into the phase lock loop passes into the phase comparator and is compared against a signal from a locked oscillator 44 and the signal is tuned by the voltage control oscillator 42 in such a manner that there is no phase differential between the signals. In the event the incoming signal changes, there would be a phase differential between the internal oscillator and the incoming signal such that an error voltage would be created and such error voltage would be used to drive the band pass filter 30. The circuitry for the phase lock loop can comprise four chips. The phase lock loop is one chip, the zero crossing detector is one chip, the band pass filter is one chip, and the amplifiers, generally two, are provided in one chip. The low pass filter 26 is a discrete LC filter.

The signal leaving the zero crossing detector is conveyed to the microprocessor 46. The pulses provided in the signal are counted by the microprocessor and compared against a standard clock and converted into a rate representative of the physiological condition, such as the respiration rate and/or heart rate. The preferred microprocessor is a CMOS microprocessor MC 146805 commercially available from Motorola, Inc. Associated with the microprocessor 46 and operatively connected thereto is a random access memory (RAM) device 60 and a read only memory (ROM) device 58. The microprocessor also has associated with it a remote patient control 52 for use by the patient. The remote patient control 52 provides an actuation signal to the microprocessor when the patient requests a delivery of medication.

A keyboard 54 can also be associated with the microprocessor. The keyboard 54 provides a means for inputting data into the microprocessor or RAM and ROM memories for the microprocessor regarding a patient's condition and/or preselected values which will function as threshold values for the particular patient. In addition, the keyboard can provide a means for inputting the incremental aliquots of medication to be delivered when the system determines that medication can be administered.

A display 56 can also be associated with the microprocessor. The display can be any convenient display device, such as a CRT video monitor LED, meter gauge, and the like. The display 56 can be used to display the patient's physiological conditions as they are monitored, the dosages of medication administered to the patient, the time intervals between such dosages, identification information regarding the particular patient, and the like.

A computer interface 62 can also be associated with the microprocessor. The computer interface 62 can provide an ability for receiving and/or supplying data regarding a plurality of patients. That is, the microprocessor can be programmed from a central computer along with other microprocessors in other medication infusion systems connected to other patients, all of which systems are controlled by a central computer based upon a particular patient's needs.

The microprocessor is also operatively connected to the motor 20 in the pump assembly. The microprocessor can be operatively connected through a drive 50 for providing a drive signal to the motor 20 to move the motor in incremental steps, thereby providing actuation of the pump assembly to deliver a preselected volume of medication. A return loop can be provided on the motor to indicate to the microprocessor when such an incremental step has occurred. Upon delivery of the preselected dosage, the microprocessor prevents any further delivery until the system again is activated.

Figure 6:
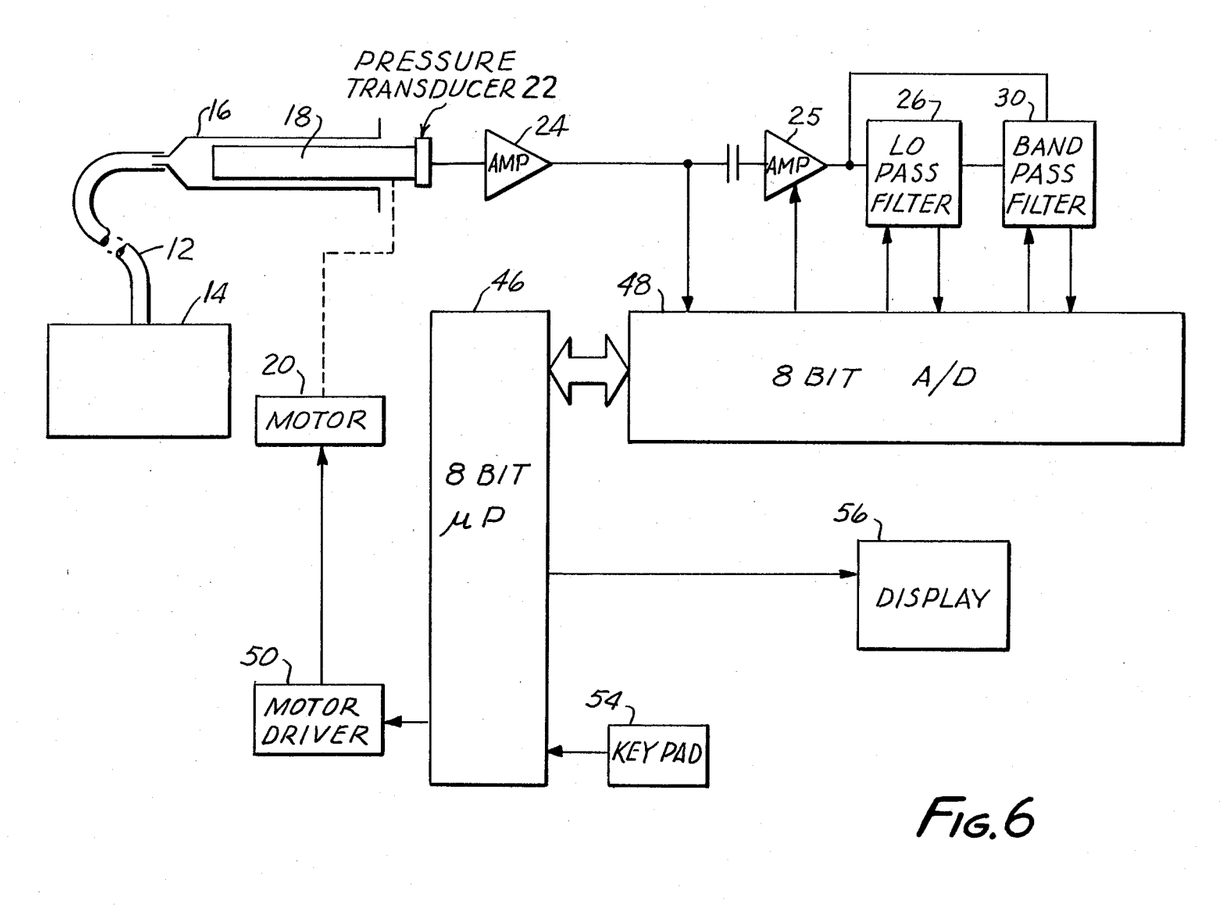
FIG. 6 is a block diagram of another circuit for the patient controlled medication infusion system.

An alternative system and its corresponding circuit is shown in FIG. 6. In FIG. 6 as in the earlier figures, similar components are given the same designation. The system in FIG. 6 takes the signal after passing from the band pass filter and passes the signal to an analog to digital converter 48. In the analog to digital converter, the signal is converted to an electric signal which is representative of the patient's physiological condition, such as respiration rate and/or heart rate. The analog to digital converter is operatively connected to the microprocessor which functions in a manner similar to the microprocessor shown in the preferred system of FIG. 1.

Figure 7:
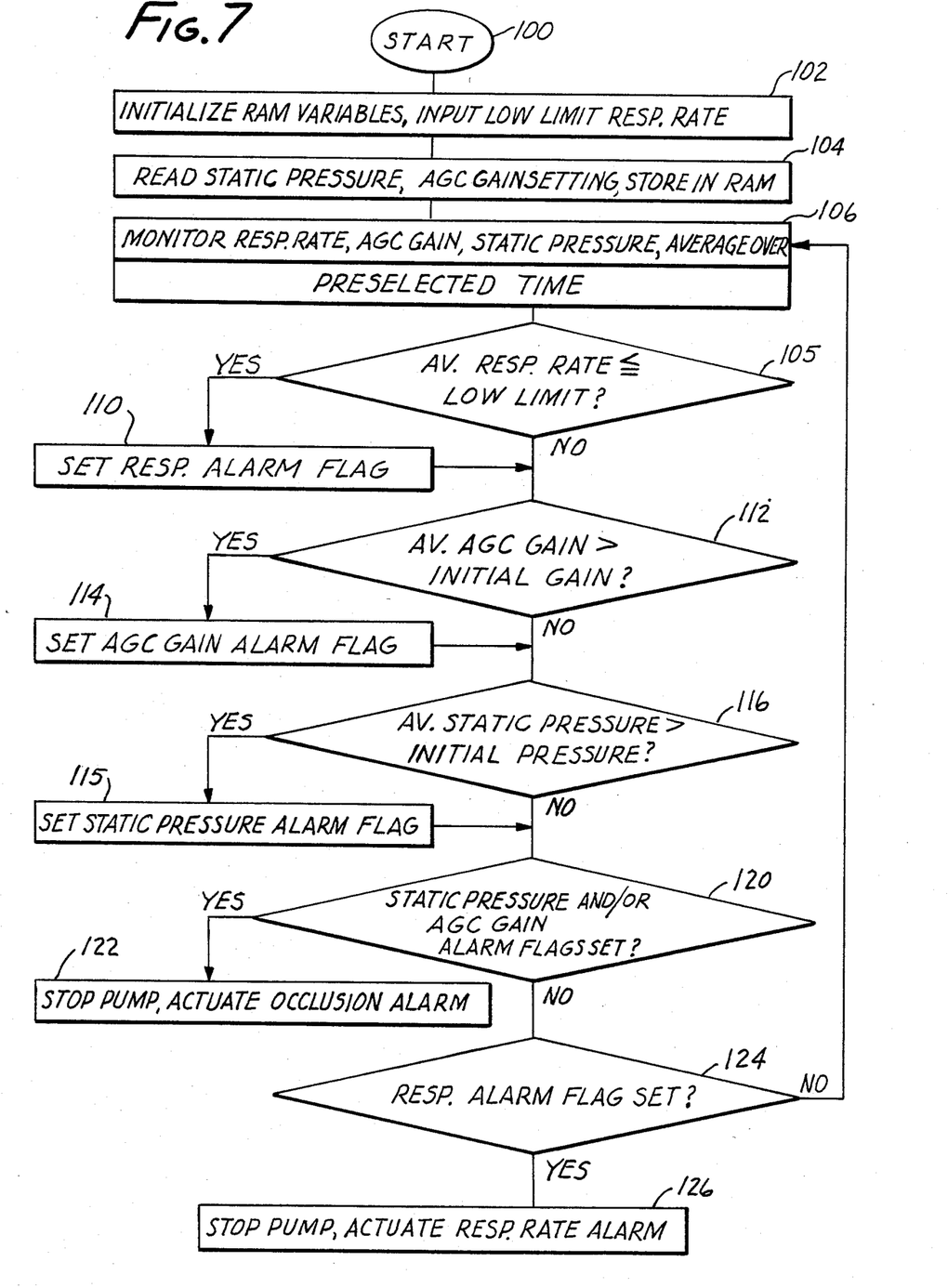
FIG. 7 is a block diagram of a logic flowchart for programming the microprocessor in the system herein.

In the preferred embodiment of the system shown in FIG. 1, the microprocessor 46 is a programmable microprocessor. FIG. 7 illustrates a logic flowchart for programming the microprocessor to carry out the functions for operating the system. Rather than describe a specific program which is, of course, limited to a single language, a programming logic flowchart is described below so that those of ordinary skill in the art can use the programming language of their choosing.

With regard to the program shown in FIG. 7, the initial programming step 102 is to initialize the RAM variables and to input the low limit respiration rate, which is the threshold respiration rate for the patient, below which medication should not be administered. The next step 104 is to read the static pressure in the infusion line and to read the AGC gain setting, which values are stored in the RAM. The next step programmed into the microprocessor is step 106 which is to monitor the physiological condition, such as the respiration rate and/or heart rate of the patient, the AGC gain, the static pressure, and to average such values over a preselected period of time, such as two minutes. Step 106 begins the cyclic monitoring loop within the microprocessor. In step 108, the determined average respiration rate is compared with the low limit respiration rate. If the average respiration rage is less than or equal to the low limit respiration rate, then step 110 is to be performed. Step 110 is the setting of a respiration rate alarm flag. If in step 108 the average respiration rate is greater than the low limit respiration rate, then the system proceeds to step 112. If the respiration alarm flag has been set in step 110, then the program also proceeds to step 112. In step 112, the average of the automatic gain control averaged over the preselected time is compared to the initial gain. If the average of the AGC gain is greater than the initial gain, then step 114 is performed which sets the AGC gain alarm flag. If the average AGC gain is less than the initial gain, then step 116 is performed. If the AGC gain alarm flag is set, then the program proceeds to step 116.

At step 116, the average static pressure over the preselected time is compared to the initial pressure. If in comparing the average static pressure and initial pressure in step 116, the average static pressure is found to be greater than the initial pressure, then the static pressure alarm flag is set in step 118. If the average static pressure is less than the initial pressure, then the program proceeds to step 120 which is also arrived at following step 118. In step 120, there is a check to determine whether the static pressure and/or AGC gain alarm flags have been set in steps 114 or 118. If the flags have been set, then step 122 is performed which stops the pump and actuates the occlusion alarm. In the event the static pressure and/or AGC gain alarm flags have been set, then that is indicative that an occlusion or infiltration of the infusion line has occurred. The system provides that an alarm be given to an attendant in such instances of occlusion or infiltration.

If in step 120 the static pressure and/or AGC gain alarm flags have not been set, then step 124 is performed which is a check to determine whether the respiration rate alarm flag had been set in step 110. If the respiration rate alarm flag had been set, then the step 126 is performed. In step 126, the pump is stopped and the respiration rate alarm is actuated to signal an attendant that the patient has a condition of depressed respiration rate. Such a state can be indicative of over medication such that no additional medication need be delivered. If in step 124 the respiration rate alarm flag had not been set, then the program returns to step 106 and the cycle is repeated.

It will be appreciated that with regard to the flowchart shown in FIG. 7, the step 102 can also include initializing the RAM by inputting a threshold or low limit heart rate. Then step 106 would include monitoring the heart rate and averaging the heart rate over a preselected time period. Subsequently, a similar comparison step as step 108 can be performed where the average heart rate is compared to the threshold heart rate limit. If the average heart rate is less than or equal to the threshold heart rate limit, then a heart rate alarm flag can be set. If the average heart rate is greater than the threshold heart rate limit, then subsequent steps such as steps 108, 112, 116 and the like can be performed. A check step similar to step 124 is also added which would check to see if the heart rate alarm flag had been set. If the heart rate alarm flag had been set in a manner similar to the respiration alarm flag having been set, then the pump could be stopped and a heart rate alarm actuated in a step similar to step 126 shown in the flowchart of FIG. 7.

Figure 8:
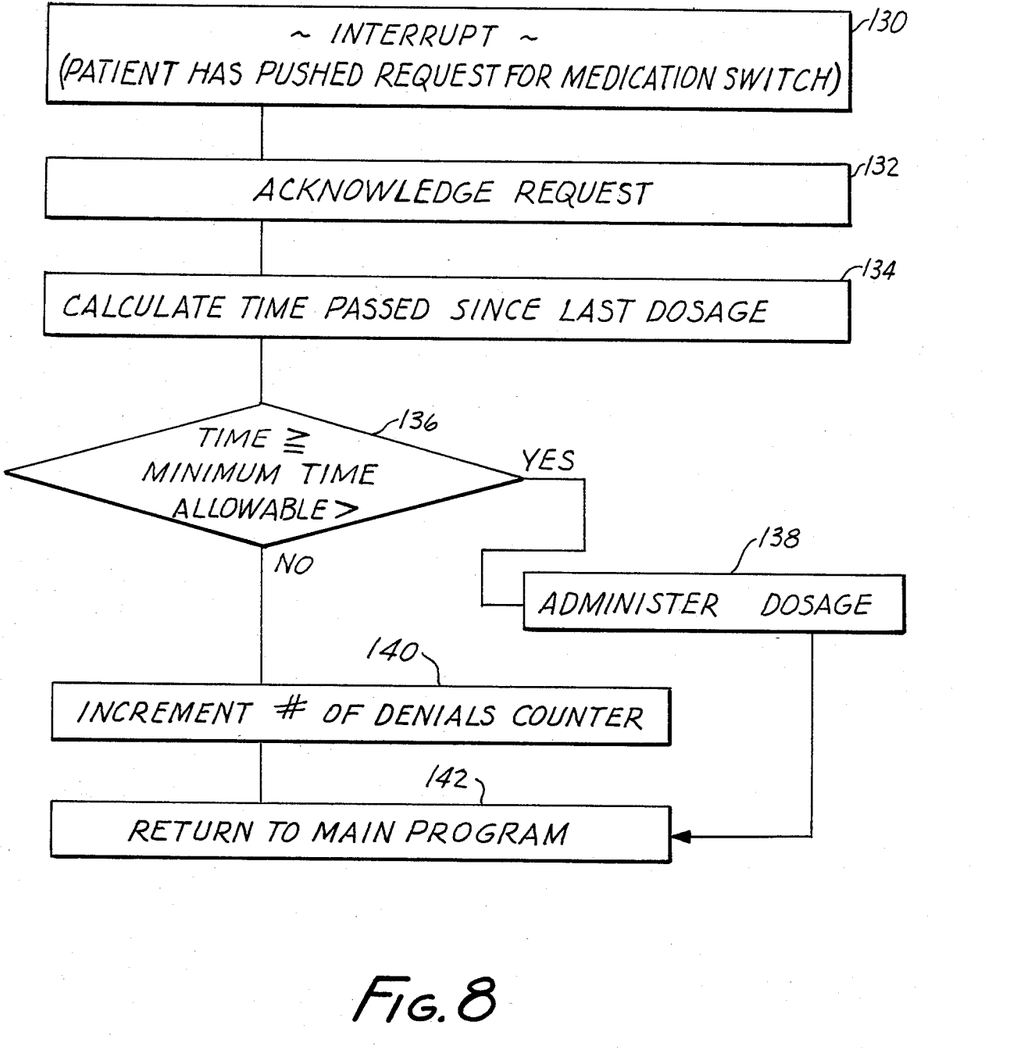
FIG. 8 is a block diagram of a flowchart showing a sequence in the systems operation.

In the integrated system that comprises the medication infusion system herein, the patient control and input to the system is represented by the flowchart shown in FIG. 8. The patient can input a demand signal for medication through the remote patient control 52 shown in FIG. 1. When the patient activates the remote control and performs step 130 of the flowchart in FIG. 8, then the cyclic program shown in FIG. 7 beginning with and returning to step 106 shown therein, is interrupted. Upon interruption of the program, the system acknowledges that a request has been made, such as by step 132. The acknowledgment of the request can be a visual acknowledgment and/or audible acknowledgement. In step 134, the system calculates the time that has elapsed since the last dosage of medication had been administered to the patient. Following the calculation in step 134, the step 136 is performed which is a comparison of the elapsed time with a minimum time allowable between dosages. The minimum time can be preprogrammed into the memory of the system. The attendant or attending physician for the patient can program in a minimum allowable time between dosages based upon the patient's medical history and the medication being administered. In step 136, the elapsed time is compared with the minimum time allowable. If the elapsed time is greater than or equal to the minimum time, then a signal can be provided to the pump assembly to provide the prescribed dosage of medication. The program then returns to the main cyclic program through step 142, which main cyclic program is shown beginning with and ending with step 106 of the program shown in FIG. 7.

If the elapsed time is less than the minimum allowable time, then the system can note and store the number of demands and/or denials for delivery of medication. The storage of such amount of denials and/or demands can be displayed for the benefit of the attendant or attending physician. Based upon such values, the program could be changed to suit the particular needs of the patient or the medication can be changed. Following storage of the information, the program can proceed to the main program as shown in step 142.

A variation of the program shown in FIG. 8 is that if the elapsed time is less than the minimum allowable time, then the demand for medication can be stored and when the elapsed time becomes greater than or equal to the minimum allowable time between dosages, then the system can provide a control order to the pump assembly to administer a dosage of medication.

The medication infusion system herein provides an improved method for delivering medication to a patient based upon the patient's perceived needs for such medication. Safeguards are built into the system by having the system capable of being preprogrammed or tuned to a particular patient's needs and physical condition. That is, the attending physician for the patient can prescribe the appropriate medication, input the dosage to be administered, minimum time between dosages, and patient's minimum respiration rate below which medication should not be administered. In addition to the respiration rate, an option is provided that the attending physician can also input a minimum heart rate below which medication should not be administered. The system, once activated, monitors the patient's physical conditions and automatically shuts down should such minimum physical conditions be detected. A benefit to the system herein is that it can also detect occlusion and/or infiltration of the infusion line in the peripheral vein. If the system detects infiltration and/or occlusion, then the system also shuts down the pump and provides an alarm. The various alarms provided by the system can signal an attendant to correct any deficiency within the administration set or infusion line or to take proper corrective measures should the physical condition of the patient be below the minimum physical conditions.

We claim:

1. A medication infusion system comprising:
   an infusion line for introducing medication to a peripheral vein of a patient;
   pump means along the infusion line for delivering medication through the infusion to the peripheral vein of the patient;
   pressure transducer means in fluid wave communication with medication in the infusion line for converting sensed fluid pressure waves to electrical signals;
   amplifier means electrically connected to the pressure transducer means for increasing the strength of the electrical signal;
   gain controlled amplifier means electrically connected to the amplifier means for maintaining the electrical signal at a predetermined amplitude regardless of the input amplitude variations of the electrical signal;
   tracking filter means electrically connected to the gain controlled amplifier means for filtering the electrical signal provided by the pressure transducer means through the gain controlled amplifier means to provide an electrical signal representative of the patient's respiration rate over a preselected full clinical respiration rate range;
   a computer means operatively connected to the tracking filter means for deriving from the electrical signal a control signal for controlling the operation of the pump means which is operatively connected to the computer means, the computer means comprising:
      means for determining the presence of an electrical signal representative of the patient's respiration rate;
      clock means for converting the electrical signal to a rate signal representative of the patient's respiration rate;
      first comparing means for comparing the rate signal with a preselected respiration rate;
      storage means for storing each rate signal; and
      incremental motor control means for providing a signal to the pump means for actuating the pump means in preselected increments when the rate signal is present and is greater than the preselected respiration rate and for providing a signal to the pump means to stop such pump means when no electrical signal is detected.

2. A medication infusion system as recited in claim 1 wherein the tracking filter means comprises a band pass filter electrically connected to the gain controlled amplifier means, a zero crossing detector electrically connected to the band pass filter, and a phase lock loop means for driving the band pass filter to provide an electrical signal representative of the patient's respiration rate.

3. A medication infusion system as recited in claim 2 wherein the phase lock loop means comprises a zero comparator electrically connected to the zero crossing detector, a low pass filter electrically connected to the zero comparator, a buffer amplifier electrically connected to the low pass filter, a voltage controlled oscillator electrically connected to the amplifier and the band pass filter, and a locked oscillator electrically connected to the voltage controlled oscillator and zero comparator.

4. A medication infusion system as recited in claim 1 further comprising a low pass filter electrically connected to the amplifier means and gain controlled amplifier means for filtering electrical noise from the signal.

5. A medication infusion system as recited in claim 1 wherein the means for determining the presence of an electrical signal comprises gain averaging means for averaging the gain applied to the signal by the gain controlled amplifier means over a preselected period of time and second comparing means for comparing the average gain applied to the initial gain which provides an indication of the presence of an electrical signal when the average gain applied is greater than the initial gain and provides an indication of a loss of electrical signal when the average gain applied is less than the initial gain.

6. A medication infusion system as recited in claim 5 further comprising alarm means operatively connected to the computer means for providing a signal when such second comparing means detects the average gain applied is greater than the initial gain.

7. A medication infusion system as recited in claim 5 wherein the means for determining the presence of an electrical signal further comprises:
   the storage means storing an initial static fluid pressure in the infusion line;
   averaging means for averaging static fluid pressure over a preselected period of time; and
   third comparing means for comparing the average static fluid pressure with the initial static fluid pressure which provides an indication of the presence of an electrical signal when the average static fluid pressure is less than the initial static fluid pressure and provides an indication of a loss of electrical signal when the average static fluid pressure is greater than the initial static fluid pressure.

8. A medication infusion system as recited in claim 7 further comprising alarm means operatively connected to the computer means for providing a signal when such third comparing means detects the average static fluid pressure is greater than the initial static fluid pressure.

9. A medication infusion system as recited in claim 1 wherein the means for determining the presence of an electrical signal comprises:
   the storage means storing an initial static fluid pressure in the infusion line;
   averaging means for averaging static fluid pressure over a preselected period of time; and
   third comparing means for comparing the average static fluid pressure with the initial static fluid pressure which provides an indication of the presence of an electrical signal when the average static fluid pressure is less than the initial static fluid pressure and provides an indication of a loss of electrical signal when the average static fluid pressure is greater than the initial static fluid pressure.

10. A medication infusion system as recited in claim 1 wherein the tracking filter means provides an electrical signal representative of the patient's respiration rate and heart rate over a preselected clinical range.

11. A medical infusion system as recited in claim 10 wherein the computer means further comprises:
   means for converting the electrical signal representative of the patient's heart rate to a heart rate signal;
   fourth comparing means for comparing the heart rate signal to a preselected heart rate; and the incremental motor control means further provides a signal to the pump means to stop the pump means when the heart rate signal is less than the preselected heart rate.

12. A medication infusion system as recited in claim 11 further comprising alarm means operatively connected to the computer means for providing a signal when such fourth comparing means detects the detected heart rate is less than the preselected heart rate.

13. A medication infusion system as recited in claim 1 further comprising alarm means operatively connected to the computer means for signaling when an absence of signal is detected by such computer means.

14. A medication infusion system as recited in claim 1 further comprising alarm means operatively connected to the computer means for providing a signal when such first comparing means detects that the rate signal is less than the preselected respiration rate.

15. A medication infusion system as recited in claim 1 wherein the computer means is programmed to derive a control signal for controlling the operation of the pump by the steps of:
comparing the electrical signal to determine if present;
if an electrical signal is absent, providing a control signal to the pump means for stopping the pump means from delivering medication;
if the electrical signal is present, then comparing the electrical signal with a preselected respiration rate;
determining whether the electrical signal is below the preselected rate;
if the electrical signal is below the preselected rate, then providing a control signal to the pump means for stopping the pump means from delivering medication;
if the electrical signal is greater than the preselected rate, then providing a control signal to the pump means for providing a predetermined dosage of medication.

16. A medication infusion system as recited in claim 15 wherein the computer means is further programmed to derive a control signal for controlling the operation of the pump by the steps of:
fifth comparing means comparing the time between the last incremental delivery of medication and the current time and comparing such time differential to a preselected time differential;
if such time differential is less than such preselected time differential, then delaying the control signal to the pump means until such time differential equals the preselected time differential;
if such time differential is greater than the preselected time differential, then providing a control signal to the pump means for delivering an aliquot of medication to the patient.

17. A medication infusion system comprising:
an infusion line for introducing medication to a peripheral vein of a patient;
pump means along the infusion line for delivering medication through the infusion line to the peripheral vein of the patient;
pressure transducer means in fluid wave communication with medication in the infusion line for converting sensed fluid pressure waves to electrical signals;
filter means electrically connected to the pressure transducer means for filtering the electrical signal provided by the pressure transducer means to provide an electrical signal representative of the patient's respiration rate;
an analog to digital converter means operatively connected to the filter means for producing digital monitor signals which are representative of the patient's respiration rate;
a computer means operatively connected to the analog to digital converter means for deriving from the digital monitor signals a control signal for controlling the operation of the pump means which is operatively connected to the computer means, the computer means comprising:
means for determining the presence or absence of a signal;
clock means for converting the digital monitor signal to a rate signal representative of the patient's respiration rate;
first comparing means for comparing the digital monitor signal with a preselected respiration rate;
second comparing means for comparing the digital monitor signal with the unfiltered electrical signal;
storage means for storing each digital monitor signal;
third comparing means for comparing the digital monitor signal with an earlier digital monitor signal stored in such storage means; and
incremental motor control means for providing a signal to the pump means for actuating the pump means in preselected increments.

18. A medication infusion system as recited in claim 17 wherein the filter means provides an electrical signal representative of the patient's respiratory rate and heart rate; the analog to digital converter means produces a first digital monitor signal representative of the patient's respiration rate and a second digital monitor signal representative of the patient's heart rate; and the computer means further comprises:
second clock means for converting the second digital monitor signal to a rate signal representative of the patient's heart rate;
fourth comparing means for comparing the second digital monitor signal with a preselected heart rate;
fifth comparing means for comparing the second digital monitor signal with the unfiltered electrical signal;
second storage for storing such second digital monitor signal; and
sixth comparing means for comparing the second digital monitor signal with an earlier second digital monitor signal stored in such second storage means.

* * * * *